US012690905B1

(12) United States Patent
Lentner et al.

(10) Patent No.: US 12,690,905 B1
(45) Date of Patent: Jul. 28, 2026

(54) POLYAXIAL LOCKING FASTENER WITH NEGATIVE THREADS

(71) Applicant: Ortho Inventions, LLC, Palm Beach Gardens, FL (US)

(72) Inventors: Greg Lentner, Maumee, OH (US); John E. Hammill, Sr., Maumee, OH (US)

(73) Assignee: Ortho Inventions, LLC, Palm Beach Gardens, FL (US)

( * ) Notice: Subject to any disclaimer, the term of this patent is extended or adjusted under 35 U.S.C. 154(b) by 0 days.

(21) Appl. No.: 19/428,476

(22) Filed: Dec. 22, 2025

(51) Int. Cl.
*A61B 17/86* (2006.01)
*A61B 17/00* (2006.01)
*A61B 17/56* (2006.01)
*A61B 17/58* (2006.01)
(Continued)

(52) U.S. Cl.
CPC ...... *A61B 17/8605* (2013.01); *A61B 17/8625* (2013.01); *A61B 17/866* (2013.01); *A61B 2017/00526* (2013.01); *A61B 2017/564* (2013.01); *A61B 17/58* (2013.01); *A61B 17/7001* (2013.01); *A61B 17/7032* (2013.01); *A61B 17/7034* (2013.01); *A61B 17/7035* (2013.01); *A61B 17/7037* (2013.01); *A61B 17/7038* (2013.01); *A61B 17/704* (2013.01); *A61B 17/7082* (2013.01); *A61B 17/7083* (2013.01); *A61B 17/84* (2013.01);
(Continued)

(58) Field of Classification Search
CPC ............ A61B 17/8605; A61B 17/8625; A61B 17/866; A61B 17/84; A61B 17/86; A61B 17/861; A61B 17/8615; A61B 17/8685; A61B 17/863; A61B 17/58; A61B 17/7001; A61B 17/7032; A61B 17/7034; A61B 17/7035; A61B 17/7037; A61B 17/704; A61B 17/7038; A61B 17/7082; A61B 17/7083; A61B 2017/564; A61B 2017/00526
USPC .............. 606/300, 305, 301, 307, 308, 309, 606/315–316, 246, 264, 265, 266–276, 606/279; 411/243, 244, 986, 91, 932
See application file for complete search history.

(56) References Cited

U.S. PATENT DOCUMENTS

2011/0098755 A1* 4/2011 Jackson ............. A61B 17/8685
606/305
2014/0214097 A1* 7/2014 Jackson ............. A61B 17/7037
606/305

* cited by examiner

*Primary Examiner* — Marcela I. Shirsat
(74) *Attorney, Agent, or Firm* — McHale & Slavin, P.A.

(57) ABSTRACT

A polyaxial ball-and-socket fastener is disclosed that provides enhanced locking performance through intersecting negative thread profiles formed on complementary hemispherical surfaces. The fastener includes a saddle assembly having a hemispherical socket with a right-hand negative thread profile and an anchor member having a spherical head with a left-hand negative thread profile. When the saddle assembly is advanced toward the anchor member, the oppositely oriented negative thread profiles intersect and counterrotate relative to one another to generate multidirectional frictional interference along the curved ball-and-socket interface. This interaction produces a strong locking effect without requiring proportionally increased torque or compressive force, while still permitting wide-range polyaxial articulation prior to tightening. The configuration increases resistance to micro-motion and cyclic loading, maintains a substantially spherical geometry for smooth pre-lock articulation, and enables controlled deformation of the thread profiles during final tightening to further enhance fixation stability.

12 Claims, 3 Drawing Sheets

(51) Int. Cl.
     *A61B 17/70*          (2006.01)
     *A61B 17/84*          (2006.01)
(52) U.S. Cl.
     CPC ............. *A61B 17/86* (2013.01); *A61B 17/863*
             (2013.01); *A61B 2017/8655* (2013.01); *A61B*
                                     *17/8685* (2013.01)

SECTION A-A

POLYAXIAL LOCKING FASTENER WITH NEGATIVE THREADS

FIELD OF THE INVENTION

The present invention relates generally to polyaxial fastening systems, and more particularly to ball-and-socket fasteners that employ intersecting negative thread profiles on complementary hemispherical surfaces to achieve controlled polyaxial articulation and enhanced locking performance.

BACKGROUND

Polyaxial fasteners, including ball-and-socket assemblies, are widely used in orthopedic fixation systems, spinal implant constructs, mechanical linkages, and other applications requiring both adjustable angular positioning and secure final locking. In many such devices, a spherical head received within a complementary socket allows multi-directional articulation during placement, after which a compressive load is applied to lock the components into a fixed orientation. Conventional polyaxial locking mechanisms typically rely on smooth spherical surfaces that are clamped together under substantial compressive force. While this approach can provide adequate fixation, it often requires high torque to achieve sufficient frictional resistance, which may lead to component deformation, wear, or inconsistent locking performance.

To address these concerns, some prior systems incorporate surface texturing, knurling, or shallow grooves on the mating surfaces to enhance friction. However, such features still rely primarily on increased compressive load to generate locking strength. High compressive forces may damage surrounding structures, induce stress concentrations, or cause undesirable settling or loosening under cyclic loading conditions. Additionally, texturing methods often provide friction along limited directions of curvature, resulting in uneven or insufficient locking stability.

Other approaches have attempted to introduce mechanical interlocks or directional teeth between the ball and socket surfaces. These mechanisms, however, frequently compromise the ability to freely articulate the ball prior to locking, or they require precise alignment of interlocking features, reducing the ease of use during implantation or assembly. They may also produce abrupt transitions from free motion to full lock, limiting the surgeon's or user's ability to make subtle adjustments.

Accordingly, there remains a need for a polyaxial fastener that provides strong, reliable locking without requiring excessive compressive force or torque; that distributes frictional engagement uniformly across the spherical interface; that maintains broad, unrestricted articulation before locking; and that resists loosening under cyclic loading without jeopardizing the structural integrity of the components. The present invention satisfies these needs by integrating intersecting negative thread profiles into complementary hemispherical surfaces, generating multidirectional micro-interferences that significantly enhance locking strength while preserving smooth articulation prior to engagement.

SUMMARY

The present invention relates to a polyaxial ball-and-socket fastener that achieves enhanced locking performance through the use of intersecting negative thread profiles formed on complementary hemispherical surfaces. The invention provides a saddle assembly having a hemispherical socket with a negative right-hand thread pattern and an anchor member having a spherical head with a negative left-hand thread pattern. When the saddle assembly is advanced toward the anchor member, the oppositely oriented negative thread profiles intersect and counter-rotate relative to one another, generating multidirectional frictional interference that securely locks the components without the need for high compressive forces or increased torque. This configuration allows the fastener to provide wide-range polyaxial articulation before tightening and firm, reliable fixation after tightening, with improved resistance to loosening under cyclic loading.

An objective of the invention is to provide an improved polyaxial fastener that maintains strong locking capability while reducing the compressive load and torque typically required for fixation.

Another objective is to create a ball-and-socket interface that utilizes intersecting negative thread patterns to generate frictional resistance across multiple directions of curvature, thereby enhancing mechanical stability.

A further objective is to preserve a full spherical geometry on both the socket and the spherical head so that broad articulation is available prior to locking, allowing easier alignment during installation.

Additional objectives include increasing resistance to micro-motion, reducing the risk of slippage under cyclic or physiological loading, enabling controlled deformation of thread profiles to enhance final locking, and providing a fastener system that is easy to manufacture using subtractive machining techniques while maintaining a smooth spherical interface.

Other objectives and advantages of this invention will become apparent from the following description taken in conjunction with the accompanying drawings, wherein are set forth, by way of illustration and example, certain embodiments of this invention. The drawings constitute a part of this specification, include exemplary embodiments of the present invention, and illustrate various objects and features thereof.

DETAILED DESCRIPTION OF THE PREFERRED EMBODIMENT

Figure 1B:
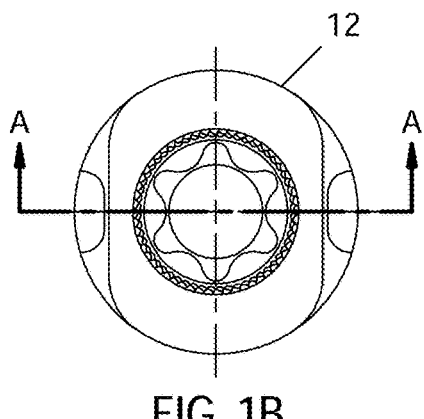
FIG. 1B is a top view thereof.
Figure 1A:
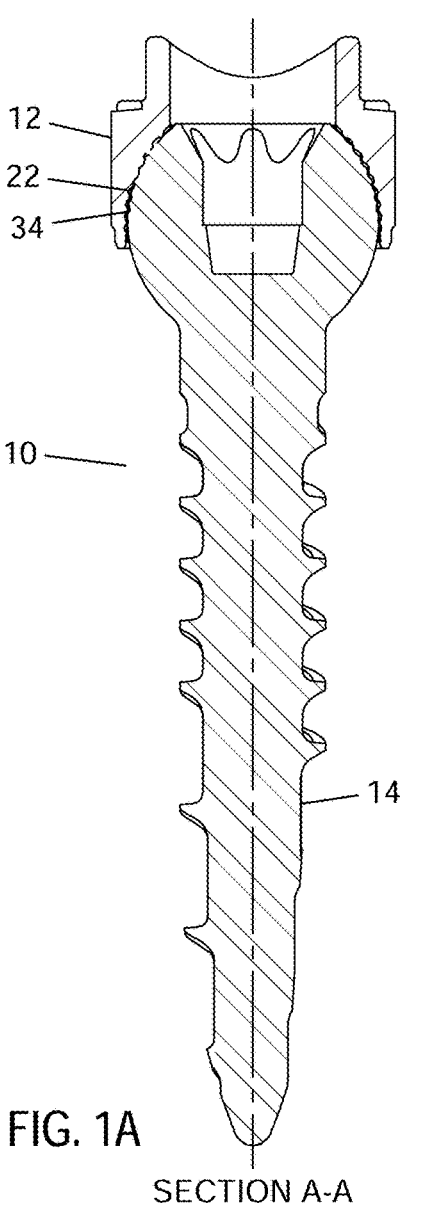
FIG. 1A is a cross sectional of an anchor and saddle.
Figure 2B:
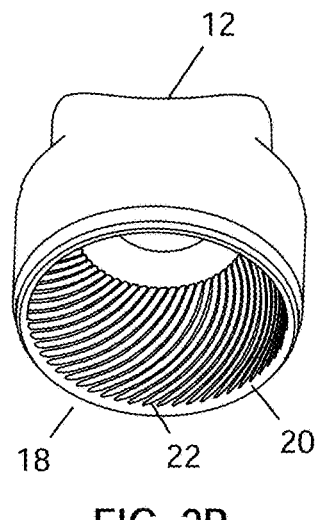
FIG. 2B is a perspective view of the saddle.
Figure 2A:
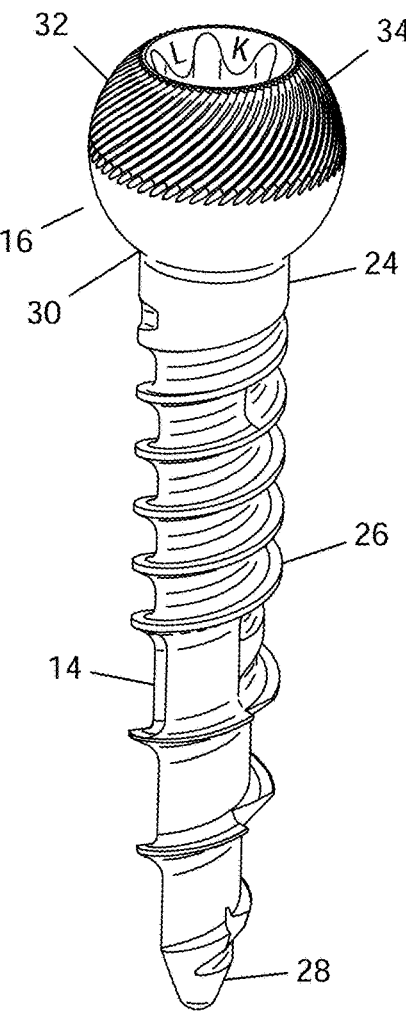
FIG. 2A is perspective view of the anchor.
Figure 3:
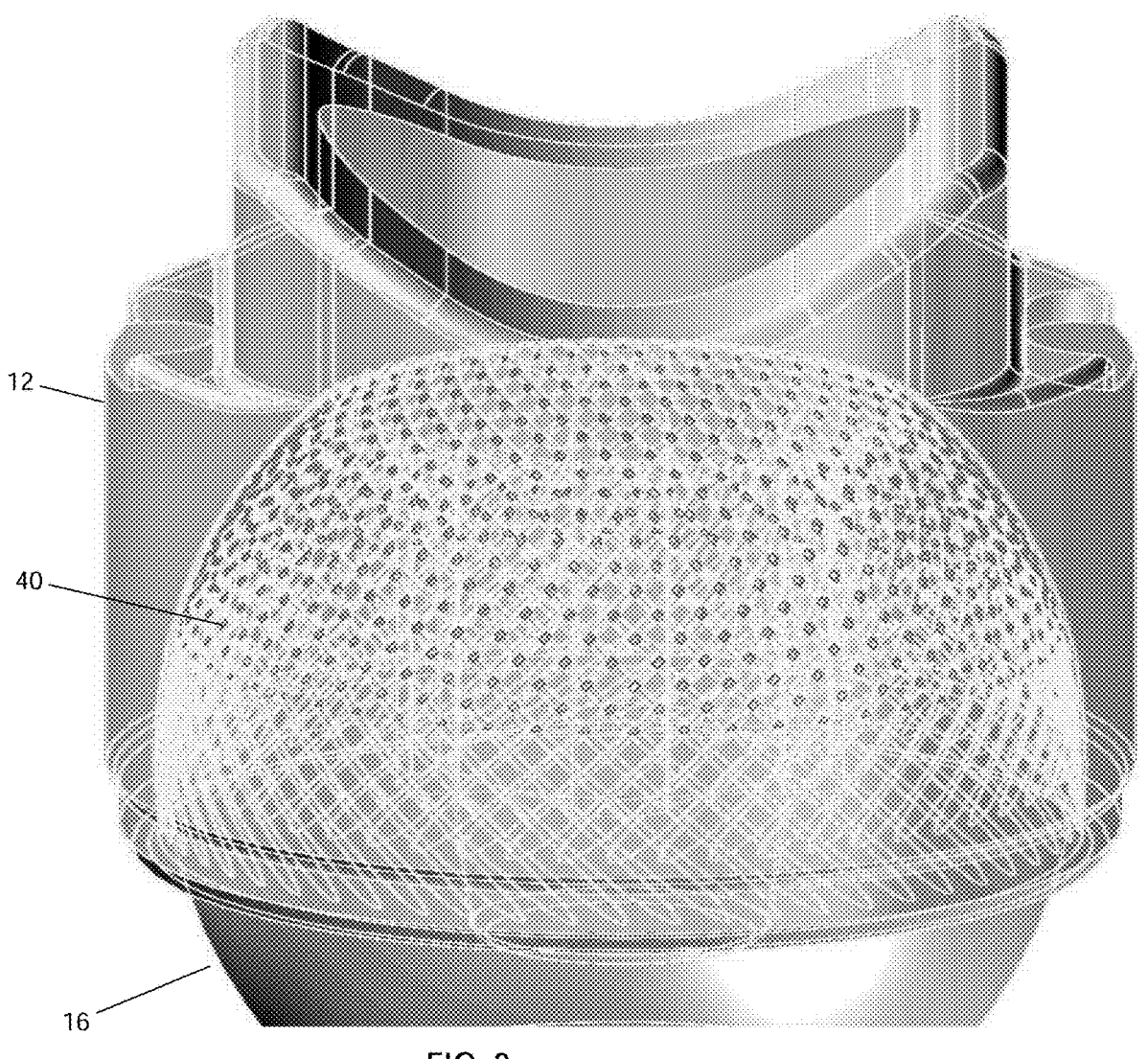
FIG. 3 is a pictorial view of the micro-interferences between the anchor and saddle.

While the present invention is susceptible of embodiments in various forms, there is shown in the drawings and will hereinafter be described a presently preferred embodiment with the understanding that the present disclosure is to be considered an exemplification of the invention and is not intended to limit the invention to the specific embodiments illustrated.

A polyaxial ball-and-socket fastener 10 is disclosed comprising a saddle assembly 12 and an anchor member 14 that cooperate to provide a controlled polyaxial interface capable of selective tightening and locking through intersecting negative thread engagement. The fastener 10 is designed so that controlled frictional interference is generated between a spherical head 16 of the anchor member 14 and a hemispherical socket 18 of the saddle assembly 12, thereby reducing the torque and compressive load typically required to achieve secure fixation.

The saddle assembly 12 includes the spherical-shaped socket 18, which is defined by a lower hemispherical surface 20. The lower hemispherical surface 20 carries a right-hand negative thread profile 22, formed by subtractive machining to remove material from the inside radius of the socket 18 while preserving its hemispherical curvature. The negative thread profile 22 may extend along a substantial portion of the hemispherical surface 20 and may exhibit a constant pitch and thread height around the circumference. In some embodiments, the hemispherical surface 20 is instead provided with a left-hand negative thread profile, with the corresponding upper hemispherical surface of the spherical head carrying a right-hand thread, as permitted by claim 12.

The anchor member 14 includes a shank 24 having bone-engaging threads 26 at a proximal end 28. The distal end 30 of the shank 24 is integrally formed with the spherical head 16, creating a monolithic structure that resists deformation under load. The spherical head 16 includes an upper hemispherical surface 32 that is machined to form a left-hand negative thread profile 34. This negative thread profile 34 is cut into the exterior of the spherical head 16 while maintaining an overall spherical geometry suitable for polyaxial articulation. The negative thread profile 34 may extend across at least fifty percent of the hemispherical surface 32 or over a greater portion where additional frictional engagement is desired.

When assembled, the spherical head 16 is received within the hemispherical socket 18, permitting free polyaxial movement prior to tightening. The geometries of the hemispherical surfaces 20 and 32 are selected to provide a polyaxial articulation range of at least twenty degrees in any direction before the onset of locking. The dimensional relationship between the spherical head 16 and the hemispherical socket 18 allows the anchor member 14 to pivot relative to the saddle assembly 12, enabling angular adjustments during placement or installation.

As the saddle assembly 12 is advanced toward the anchor member 14, such as through a compression element or driver (not shown), the right-hand negative thread profile 22 of the hemispherical surface 20 and the left-hand negative thread profile 34 of the upper hemispherical surface 32 intersect and counter-rotate relative to one another. The opposed thread directions ensure that tightening motion draws the thread profiles into mutual interference rather than allowing them to run freely along one another. The crossing of these thread geometries generates micro-interferences 40 distributed along multiple directions of the curved surfaces. These interferences 40 substantially increase friction between the spherical head 16 and the socket 18 without requiring proportional increases in torque or compressive force. A test regarding the frictional retention and resistance was performed using an independent static flexion/extension test comparing a polyaxial locking fastener without negatives threads to a polyaxial locking fastener incorporating negative threads in accordance with the present invention. The testing was performed in accordance with ASTF-179-14 to evaluate tightening torque, yield load, and yield moment. The results are summarized as: without negative threads the locking fastener using a tightening torque of 80 in-lb produced a yield load of 282 N and a yield moment of 7.0 N-m; with negative threads the locking fastener using a tightening torque of 80 in-lb produced a yield load of 532 N and a yield moment 13.3 N-m; with negative threads the locking fastener using a tightening togue of 40 in-lb produced a yield load of 333 N and a yield moment of 8.3 N-m. The test data confirms that the polyaxial locking fastener incorporating negative threads and tightened to 80 in-lb exhibits nearly a two-fold increase in yield load compared to the polyaxial locking fastener without negative threads tightened to the same torque. The data further demonstrate that the polyaxial locking fastener incorporating negative threads and tightened to only 40 in-lb achieve a yield load approximately 1.2 times greater than that of the polyaxial locking fastener without negative threads tightened to 80 in-lb. This increased "grip strength" allows a surgeon to apply approximately half the tightening torque while achieving equal or superior fixation and resistance to flexion/extension loading. These interferences 40 substantially increase friction between the spherical head 16 and the socket 18 without requiring proportional increase in torque or compressive force.

The matched pitch and thread height of the negative thread profiles 22 and 34 promote smooth engagement during advancement and consistent locking performance across the interface. In some embodiments, either or both thread profiles are configured to deform in a controlled manner when final locking torque is applied, further increasing the frictional retention and resistance to slippage under cyclic loading conditions. Such controlled deformation may occur at the thread crests or flanks and is facilitated by the negative thread geometry, which distributes stress along a broad area of the curved hemispherical surfaces.

The combination of intersecting thread profiles 22 and 34 enhances locking efficiency even when the applied compressive load is reduced by thirty percent or more compared to non-threaded ball-and-socket fasteners. The increased normal force generated by the intersecting thread engagement improves resistance to micro-motion at the interface, thereby enhancing stability under physiological or mechanical cyclic loading.

The geometry of the hemispherical socket 18, including its diameter and curvature, is selected to permit unrestricted or substantially unrestricted polyaxial articulation of the spherical head 16 until compression begins to draw the thread profiles 22 and 34 into engagement. This ensures ease of alignment and positioning before fixation is finalized. The result is a fastener 10 that provides polyaxial adjustability, controlled frictional locking, reduced torque requirements, and improved resistance to loosening, making it suitable for orthopedic, spinal, mechanical, and other applications requiring secure adjustable fixation.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs.

One skilled in the art will readily appreciate that the present invention is well adapted to carry out the objectives and obtain the ends and advantages mentioned, as well as those inherent therein. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A polyaxial ball-and-socket fastener comprising:
a saddle assembly including a spherical shaped socket with a lower hemispherical surface with a right hand thread profile that is negative to the inside radius surface of the socket;
an anchor member having a shank with bone threads at a proximal end and a spherical head integrally formed at a distal end having an upper hemispherical surface with a left hand thread profile that is negative to the outside surface of the spherical head; and
wherein the left-hand thread profile of the upper hemispherical surface of the spherical head and the right-hand thread profile of the lower hemispherical surface of the socket intersect and counter-rotate relative to one another as the saddle member is advanced toward the anchor member, such that the oppositely oriented negative thread profiles generate an increased frictional interference at the ball-and-socket interface without requiring a proportionally increased torque or compressive clamping load.

2. The polyaxial ball-and-socket fastener of claim 1, wherein the left-hand negative thread profile on the spherical head and the right-hand negative thread profile on the socket each exhibit a substantially constant pitch along their respective hemispherical circumferences.

3. The polyaxial ball-and-socket fastener of claim 1, wherein the right-hand and left-hand negative thread profiles are formed with matching pitch and thread height to promote efficient intersecting engagement during advancement of the saddle member toward the anchor member.

4. The polyaxial ball-and-socket fastener of claim 1, wherein the negative left-hand thread profile extends over at least fifty percent of the upper hemispherical surface of the spherical head.

5. The polyaxial ball-and-socket fastener of claim 1, wherein the intersecting negative thread profiles permit a polyaxial range of motion of at least twenty degrees in any direction prior to initiation of locking engagement.

6. The polyaxial ball-and-socket fastener of claim 1, wherein the intersecting thread engagement increases the normal force between the socket and the spherical head as compressive load is applied, thereby enhancing resistance to slippage under cyclic loading.

7. The polyaxial ball-and-socket fastener of claim 1, wherein at least one of the negative thread profiles is configured to undergo controlled deformation during final locking to further increase frictional retention without requiring additional torque.

8. The polyaxial ball-and-socket fastener of claim 1, wherein the left-hand negative thread profile on the spherical head is produced by subtractive machining while maintaining a substantially spherical exterior geometry.

9. The polyaxial ball-and-socket fastener of claim 1, wherein the right-hand negative thread profile of the socket is formed as an internal subtractive thread pattern that preserves the hemispherical curvature of the socket.

10. The polyaxial ball-and-socket fastener of claim 1, wherein the intersecting thread profiles generate multidirectional micro-interferences that supplement locking performance even when the compressive load is reduced by at least thirty percent.

11. The polyaxial ball-and-socket fastener of claim 1, wherein the hemispherical socket is dimensioned to permit substantially unrestricted polyaxial articulation until the saddle member is torqued to initiate intersecting thread engagement.

12. The polyaxial ball-and-socket fastener of claim 1, wherein said lower hermispherical surface is a left hand thread and said upper hermispherical surface is a right hand thread.

* * * * *